US006899729B1

(12) United States Patent
Cox et al.

(10) Patent No.: US 6,899,729 B1
(45) Date of Patent: May 31, 2005

(54) STENT FOR TREATING VULNERABLE PLAQUE

(75) Inventors: Daniel L. Cox, Palo Alto, CA (US); Christopher Feezor, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 34 days.

(21) Appl. No.: 10/322,350

(22) Filed: Dec. 18, 2002

(51) Int. Cl.[7] .................................................. A61F 2/06
(52) U.S. Cl. .................... 623/1.13; 623/1.16; 623/1.17; 606/200
(58) Field of Search ............................ 623/1.13, 1.14, 623/1.15, 1.16, 1.17, 1.31, 1.3, 1.1; 606/200

(56) References Cited

U.S. PATENT DOCUMENTS

| | | |
|---|---|---|
| 2,701,559 A | 2/1955 | Cooper |
| 3,105,492 A | 10/1963 | Jeckel |
| 3,657,744 A | 4/1972 | Ersek |
| 3,868,956 A | 3/1975 | Alfidi et al. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |

(Continued)

FOREIGN PATENT DOCUMENTS

DE  3640745 A1  6/1987

(Continued)

OTHER PUBLICATIONS

Dotter, Charles T. *Transluminally Placed Coilspring Endarterial Tube Grafts*, Investigative Radiology, pp. 329-332, Sep./Oct. 1969.

Dotter, Charles T., *Transluminal Expandable Nitinol Coil Stent Grafting: Preliminary Report*, Radiology Journal, pp. 259-260, Apr. 1983.

Cragg et al., *Non-Surgical Placement of Arterial Endoprostheses: A New Technique Using Nitinol Wire*, Radiology Journal, pp. 261-263, Apr. 1983.

(Continued)

*Primary Examiner*—Corrine McDermott
*Assistant Examiner*—Thomas J Sweet
(74) *Attorney, Agent, or Firm*—Fulwider Patton Lee & Utecht, LLP

(57) ABSTRACT

An intravascular stent is configured for asymmetrical differential deployment and to align with a fibrous cap to treat vulnerable plaque. The stent is configured so that reduced expansion forces are imparted during deployment to the fibrous cap, thereby reducing the likelihood of cap rupture. The stent includes cylindrical rings connected by links and a cover attached to a portion of the stent to differentially restrict stent expansion when the stent is expanded from a delivery diameter to an implanted diameter thereby creating asymmetrical circumferential deployment. The portion of the stent having the cover imparts lower expansion forces from the stent expansion onto the fibrous cap area than other portions of the stent not having the cover.

24 Claims, 10 Drawing Sheets

U.S. PATENT DOCUMENTS

| | | |
|---|---|---|
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,022,560 A | 6/1991 | Campbell |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |
| 5,449,373 A | 9/1995 | Pinchasik et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A | 5/1996 | Lau et al. |
| 5,545,132 A | 8/1996 | Fagan et al. |
| 5,571,135 A | 11/1996 | Fraser et al. |
| 5,591,223 A * | 1/1997 | Lock et al. ................ 623/1.17 |
| 5,603,721 A | 2/1997 | Lau et al. |
| 5,609,628 A * | 3/1997 | Keranen .................... 623/1.13 |
| 5,626,604 A | 5/1997 | Cottone, Jr. |
| 5,653,690 A | 8/1997 | Booth et al. |
| 5,653,691 A | 8/1997 | Rupp et al. |
| 5,653,727 A | 8/1997 | Wiktor |
| 5,716,396 A | 2/1998 | Williams, Jr. |
| 5,720,726 A | 2/1998 | Marcadis et al. |
| 5,733,303 A | 3/1998 | Israel et al. |
| 5,733,325 A | 3/1998 | Robinson et al. |
| 5,735,893 A | 4/1998 | Lau et al. |
| 5,782,855 A | 7/1998 | Lau et al. |
| 5,800,521 A | 9/1998 | Orth |
| 5,810,871 A | 9/1998 | Tuckey et al. |

| | | | |
|---|---|---|---|
| 5,817,152 A | 10/1998 | Birdsall et al. | |
| 5,830,217 A | 11/1998 | Ryan | |
| 5,836,965 A | 11/1998 | Jendersee et al. | |
| 5,876,419 A * | 3/1999 | Carpenter et al. | 623/1.16 |
| 5,893,852 A | 4/1999 | Morales | |
| 5,902,332 A | 5/1999 | Schatz | |
| 5,924,997 A | 7/1999 | Campbell | |
| 5,951,599 A * | 9/1999 | McCrory | 606/108 |
| 5,984,964 A | 11/1999 | Roberts et al. | |
| 5,997,468 A | 12/1999 | Wolff et al. | |
| 6,030,413 A | 2/2000 | Lazarus | |
| 6,066,168 A | 5/2000 | Lau et al. | |
| 6,146,358 A | 11/2000 | Rowe | |
| 6,231,597 B1 * | 5/2001 | Deem et al. | 623/1.12 |
| 6,245,026 B1 | 6/2001 | Campbell et al. | |
| 6,261,305 B1 * | 7/2001 | Marotta et al. | 606/200 |
| 6,348,063 B1 * | 2/2002 | Yassour et al. | 606/200 |
| 6,450,971 B1 | 9/2002 | Andrus et al. | |
| 6,451,044 B1 | 9/2002 | Naghavi et al. | |
| 6,673,089 B1 * | 1/2004 | Yassour et al. | 606/200 |
| 2001/0047138 A1 | 11/2001 | Kokate et al. | |
| 2002/0009535 A1 | 1/2002 | Michal et al. | |
| 2002/0062147 A1 | 5/2002 | Yang | |
| 2002/0077564 A1 | 6/2002 | Campbell et al. | |
| 2002/0082515 A1 | 6/2002 | Campbell et al. | |
| 2002/0091436 A1 | 7/2002 | Phelps et al. | |
| 2002/0099406 A1 | 7/2002 | St. Germain | |
| 2002/0198592 A1 * | 12/2002 | Wallace et al. | 623/1.15 |
| 2003/0078647 A1 | 4/2003 | Vallana et al. | |

FOREIGN PATENT DOCUMENTS

| | | |
|---|---|---|
| DE | 3823060 A1 | 1/1989 |
| EP | 0 062 300 A2 | 10/1982 |
| EP | 0 221 570 A2 | 5/1987 |
| EP | 0 338 816 A2 | 10/1989 |
| EP | 0 361 192 A3 | 4/1990 |
| EP | 0 364 787 A1 | 4/1990 |
| EP | 0 372 789 A3 | 6/1990 |
| EP | 0 380 668 A1 | 8/1990 |
| EP | 0 407 951 A3 | 1/1991 |
| EP | 9 408 245 A1 | 1/1991 |
| EP | 0 421 729 A2 | 4/1991 |
| EP | 0 423 916 A1 | 4/1991 |
| EP | 0 428 479 A1 | 5/1991 |
| EP | 0 517 075 B1 | 12/1992 |
| EP | 0 540 290 A2 | 5/1993 |
| EP | 0 541 443 A1 | 5/1993 |
| EP | 0 807 424 A2 | 11/1997 |
| FR | 2 677 872 | 12/1992 |
| GB | 2 070 490 A | 9/1981 |
| GB | 2 135 585 A | 11/1983 |
| JP | 58-501458 | 9/1983 |
| JP | 62-213762 | 9/1987 |
| JP | 62-231657 | 10/1987 |
| JP | 62-235496 A | 10/1987 |
| JP | 63-214264 | 9/1988 |
| JP | 63-246178 | 10/1988 |
| JP | 01083685 A | 3/1989 |
| JP | 1-299550 | 12/1989 |
| JP | 2-174859 | 7/1990 |
| JP | 2 255157 | 10/1990 |
| JP | 03009745 A | 1/1991 |
| JP | 03009746 A | 1/1991 |
| JP | 3-57465 | 3/1991 |
| JP | 3-151983 | 6/1991 |
| JP | 4-25755 | 2/1992 |
| WO | WO 89/01798 | 3/1989 |
| WO | WO 89/08433 | 9/1989 |
| WO | WO 91/07139 | 5/1991 |
| WO | WO 92/06734 | 4/1992 |
| WO | WO 92/09246 | 6/1992 |

OTHER PUBLICATIONS

Maass, et al., *Radiological Follow-Up of Transluminally Inserted Vascular Endoprostheses: An Experimental Study Using Expanding Spirals, Radiology Journal*, pp. 659-663, 1984.

C.R. Bard, *PE Plus Peripheral Balloon Dilation Catheter,* C.R. Bard, Inc., Aug. 1985.

Wright, et al., *Percutaneous Endovascular Stents: An Experimental Evaluation, Radiology Journal*, pp. 69-72, 1985.

Palmaz et al., *Expandable Intraluminal Graft: A Preliminary Study, Radiology Journal*, pp. 73-77, 1985.

Duprat et al., *Flexible Balloon-Expanded Stent for Small Vessels, Radiology Journal*, pp. 276-278 (1987).

Yoshioka et al., *Self-Expanding Endovascular Graft: An Experimental Study in Dogs, American Journal of Roentgeriology*, pp. 673-676, vol. 151, Oct. 1988.

Rosch, Jr., M.D. et al., *Transjugular Intrahepatic Portacaval Shunt: An Experimental Work, The American Journal of Surgery*, pp. 588-592, vol. 121, May 1971.

70th *Scientific Assembly and Annual Meeting: Scientific Program, Radiology*, Washington, D.C., Nov. 25-30, 1984, special Edition, vol. 153(P).

Charnsangavcj, D., M.D. et al., *Endovascular Stent for Use in Aortic Dissection: An In Vitro Experiment, Radiology*, pp. 323-324, vol. 157, No. 2, Nov. 1985.

72nd *Scientific Assembly and Annual Meeting: RSNA Scientific Program, Radiology*, Chicago: Nov. 30-Dec. 5, 1986, Special Edition, vol. 161(P).

Wallace, Michael J., et al., *Tracheobronchia Tree: Expandable Metallic Stents Used in Experimental and Clinical Applications (Work in Progress), Radiology*, pp. 309-312, vol. 158, Feb. 1986.

*Program: Day 2 (Nov. 18) The Radological Society of North America, Radiology,* Chicago: Nov. 30-Dec. 5, 1986, Special Edition, vol. 161(P).

Charnsangavcj, Chusilp, M.D., et al., *Stenosis of the Vena Cava: Preliminary Assessment of Treatment with Expandable Metallic Stents, Radiology*, pp. 295-298, vol. 161, Nov. 1986.

Rosch, Josef, M.D., et al., *Experimental Intrahepatic Portacaval Anastomosis: Use of Expandable Gianturco Stents, Radiology,* pp. 481-485, vol. 162, Feb. 1987.

Rosch, Josef, M.D., et al., *Gianturco Expandable Stents in Experimental and Clinical Use,* paper presented at The Twelfth Annual Course on "Diagnostic Angiography and Interventional Radiology" Mar. 23-26, 1987 (Pittsburgh, Pennsylvania).

Finci, Leo, M.D., et al., *Percutaneous Transluminal Coronary Angioplasty of a Bifurcation Narrowing Using the Kissing Wire Monorail Balloon Technique, The American Journal of Cardiology*, pp. 375-376, vol. 60, Aug. 1987.

Lawrence, David D., Jr., M.D., et al., *Percutaneous Endovascular Graft: Experimental Evaluation, Radiology,* pp. 357-360, vol. 163, May 1987.

Rosch, Josef, M.D., et al., *Gianturco Expandable Wire Stents in the Treatment of Superior Vena Cava Syndrome Recurring after Maximum-Tolerance Radiation, Cancer,* pp. 1243-1246, vol. 60, Sep. 1987.

Bonzel, T., et al., *The Sliding Rail System (Monorail): Descriptionof a New Technique for Intravascular Instrumentation and Its Application to Coronary Angioplasty, Kardiologic,* Supplement 6, pp. 119-122, 1987.

Rosch, Josef, M.D., et al., *Modified Gianturco Expandable Wire Stents in Experimental and Clinical Use*, Annales de Radiologie, pp. 100-103, vol. 31, No. 2, 1988.

Yoshioka et al., *Development and Clinical Application of Biliary Endoprosthesis Using Expandable Metallic Stents*, Japan Radiological Society, 1988, vol. 48, No. 9, pp. 1183-1185 (with translaton).

Mirich, et al., *Percutaneously Placed Endovascular Grafts for Aoertic Aneurysms: Feasibility Study*, Radiology, 1989, part 2, pp. 1033-1037.

Furui, Shigeru, M.D., et al., *Hepatic Inferior Vena Cava Obstruction: Treatment of Two Types with Gianturco Expandable Metallic Stents*, Radiology, pp. 665-670, Sep. 1990.

Kaltenbach, M., Prof. Dr., Abstracts, *Zeitschrift fur Kardiologie*, Apr. 3, 1991 (Germany only).

van der Geissen, Willem J., et al., *Coronary Stenting with a New, Radiopaque Balloon-Expandable Endoprosthesis in Pigs*, Circulation, vol. 83, No. 5, pp. 93-149, May 1991.

Strupp, G., et al., *Clinical and Angiographic Short and Medium Term Results after Coronary Stenting*, Zielschrift fur Kardiologie, Sep. 9, 1992 (German with English language summary).

Harrington, J.D., et al., *The Palmaz-Schatz Stent*, Handbook of Cardiovascular Interventions/Vascular Internventions, pp. 563-572 (undated).

* cited by examiner

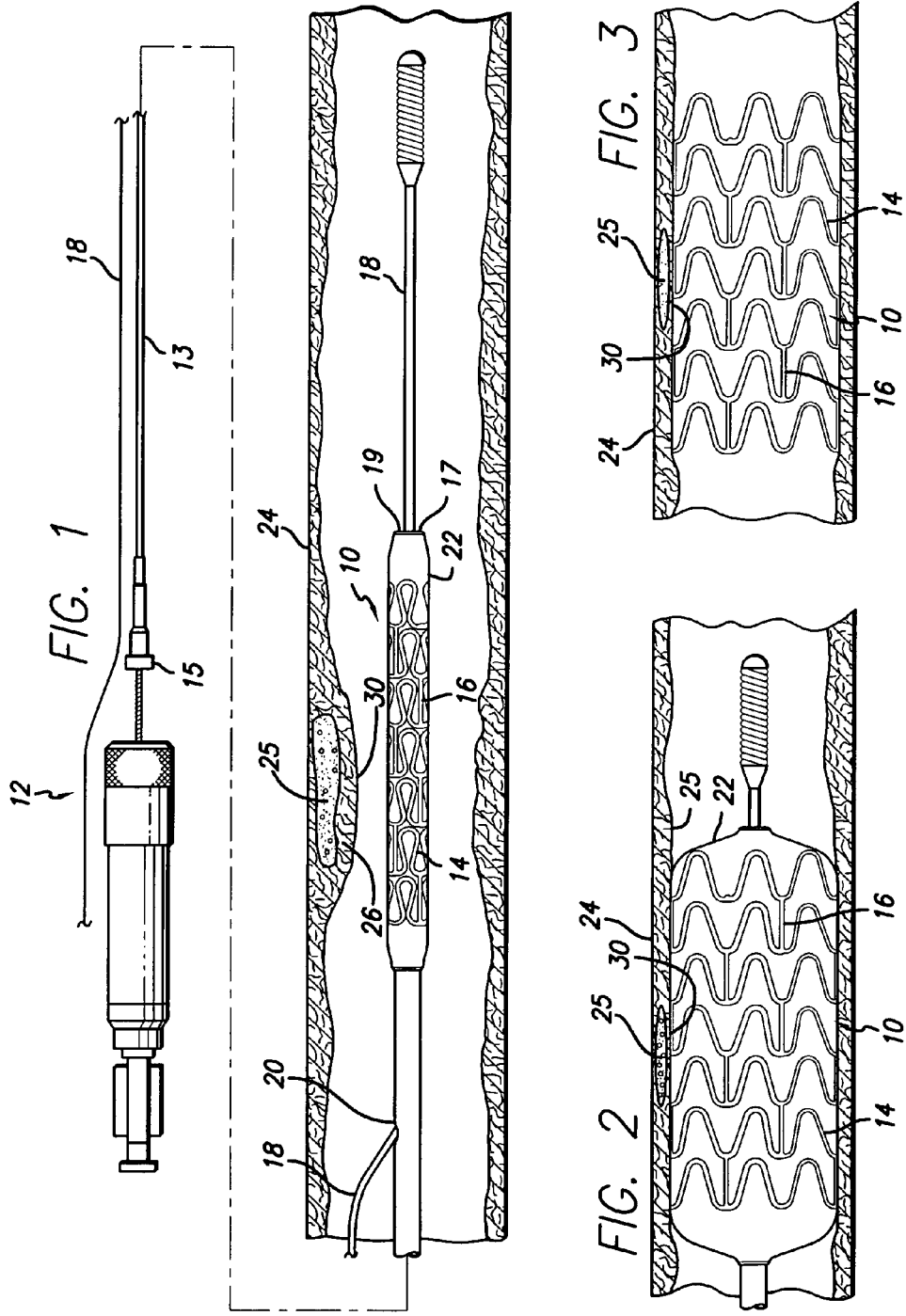

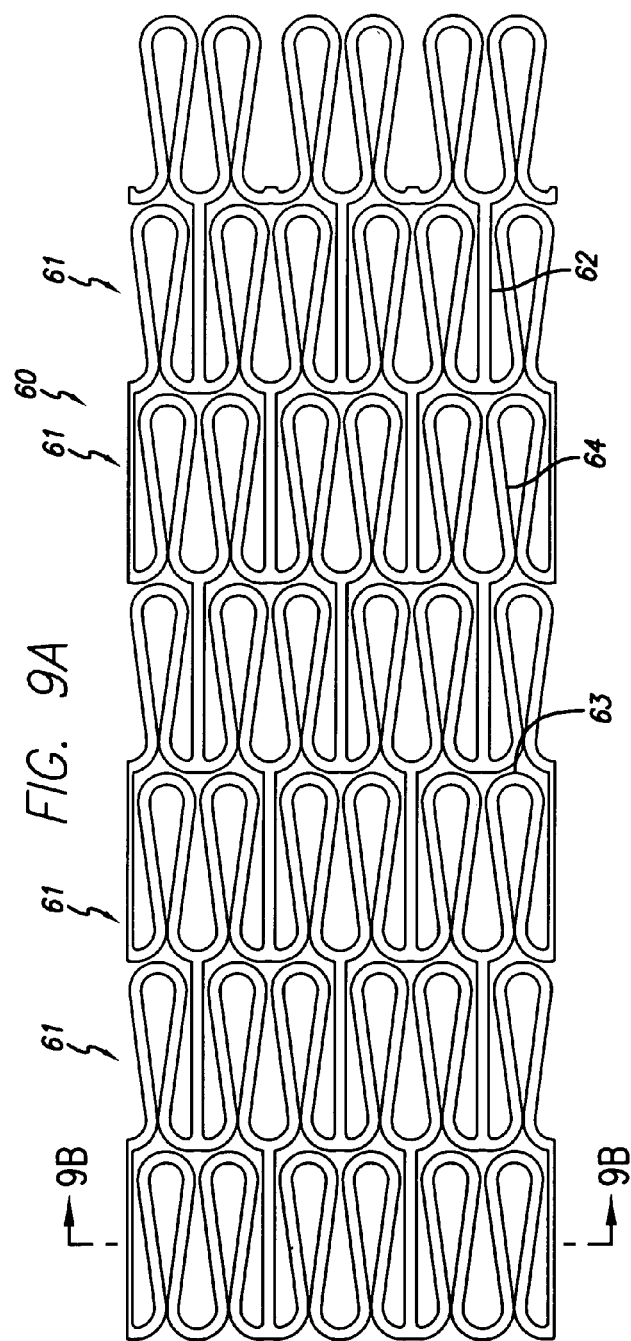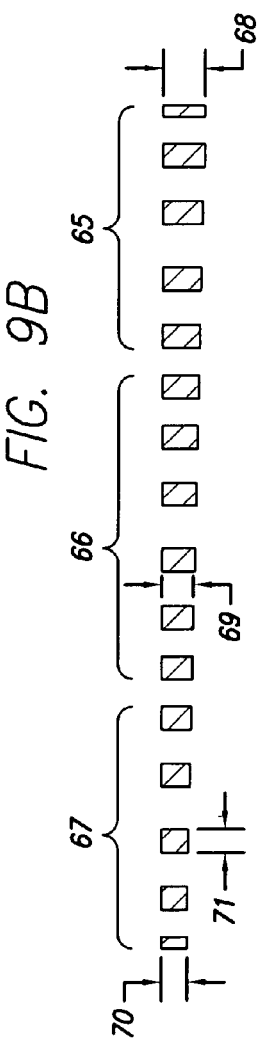

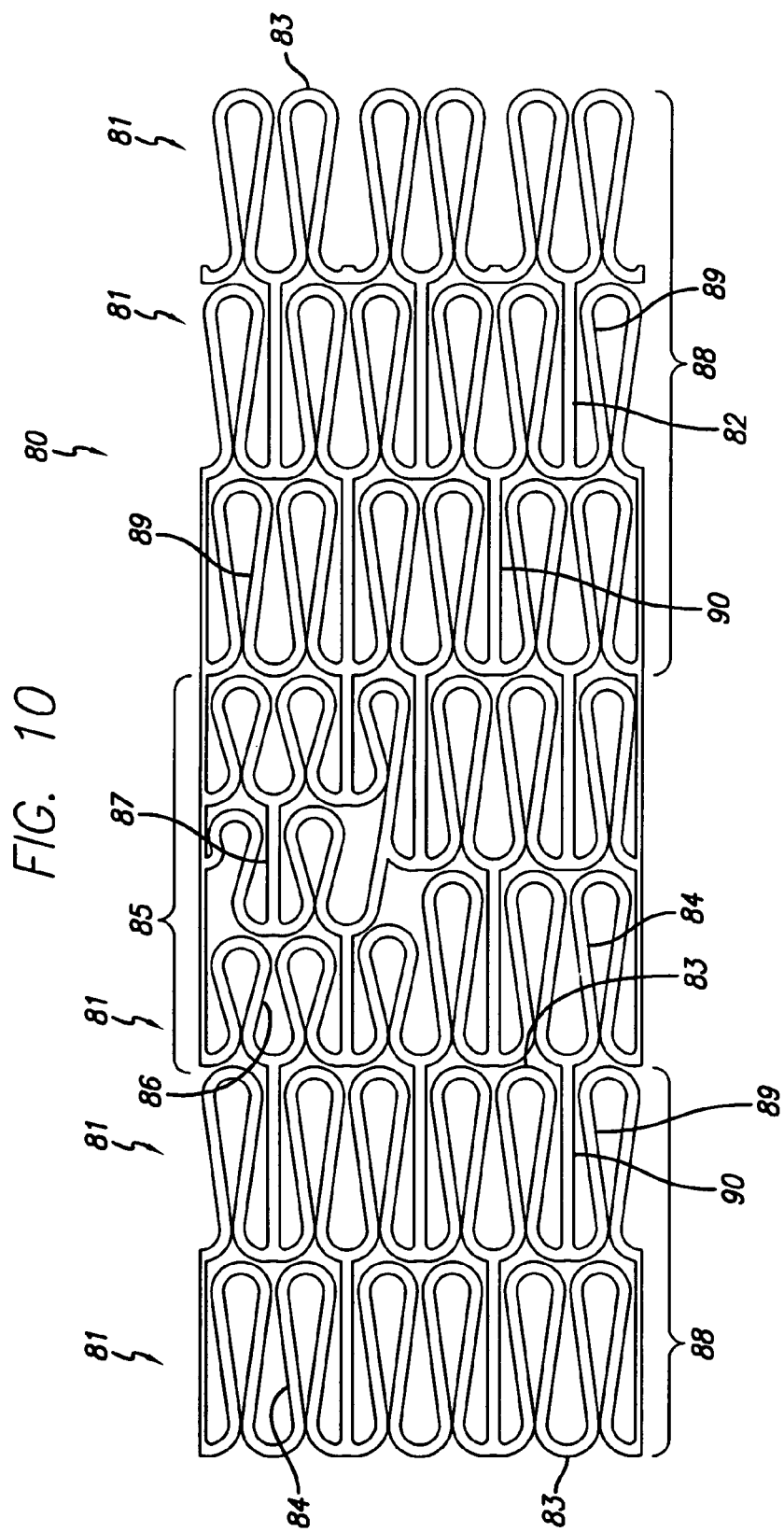

STENT FOR TREATING VULNERABLE PLAQUE

BACKGROUND OF THE INVENTION

The present invention relates to vascular repair devices, and in particular to intravascular stents, which are adapted to be implanted into a patient's body lumen, such as a blood vessel or coronary artery, for the treatment of unstable or vulnerable, human atherosclerotic plaque.

Currently, the treatment of unstable or vulnerable plaque presents a significant therapeutic challenge to medical investigators. Vulnerable plaque is characterized by a basic lesion which is a raised plaque beneath the innermost arterial layer, the intima. Atherosclerotic plaques are primarily composed of varying amounts of long chain extracellular matrix (ECM) proteins that are synthesized by smooth muscle cells. The other primary lesion component of atherosclerotic plaque includes lipoproteins, existing both extracellularly and within foam cells derived primarily from lipid-laden macrophages. In a more advanced lesion, a necrotic core may develop, consisting of lipids, foam cells, cell debris, and cholesterol crystals, and myxomatous configurations with crystalline lipid forms.

The necrotic core is rich in tissue factor and quite thrombogenic, but in the stable plaque it is protected from the luminal blood flow by a robust fibrous cap composed primarily of long chain ECM proteins, such as elastin and collagen, which maintain the strength of the fibrous cap. The aforementioned plaque represents the most common form of vulnerable plaque, known as a fibroatheroma. Histology studies from autopsy suggest this form constitutes the majority of vulnerable plaques in humans. A second form of vulnerable plaque represents a smaller fraction of the total, and these are known as erosive plaques. Erosive plaques generally have a smaller content of lipid, a larger fibrous tissue content, and varying concentrations of proteoglycans. Various morphologic features that have been associated with vulnerable plaque, include thinned or eroded fibrous caps or luminal surfaces, lesion eccentricity, proximity of constituents having very different structural moduli, and the consistency and distribution of lipid accumulations. With the rupture of fibroatheroma forms of vulnerable plaque, the luminal blood becomes exposed to tissue factor, a highly thrombogenic core material, which can result in total thrombotic occlusion of the artery. In the erosive form of vulnerable plaque, mechanisms of thrombosis are less understood but may still yield total thrombotic occlusion.

Although rupture of the fibrous cap in a fibroatheroma is a major cause of myocardial infarction (MI) related deaths, there are currently no therapeutic strategies in place to treat lesions that could lead to acute MI. The ability to detect vulnerable plaques and to treat them successfully with interventional techniques before acute MI occurs has long been an elusive goal. Numerous finite element analysis (FEA) studies have proved that, in the presence of a soft lipid core, the fibrous cap shows regions of high stresses. Representative of these studies include the following research articles, each of which are incorporated in their entirety by reference herein: Richardson et al. (1989), Influence of Plaque Configuration and Stress Distribution on Fissuring of Coronary Atherosclerotic Plaques, Lancet, 2(8669), 941–944; Loree et al. (1992), Effects of Fibrous Cap Thickness on Circumferential Stress in Model Atherosclerotic Vessels, Circulation Research, 71, 850–858; Cheng et al. (1992), Distribution of Circumferential Stress in Ruptured and Stable Atherosclerotic Lesions: A Structural Analysis With Histopathological Correlation, Circulation, 87, 1179–1187; Veress et al. (1993), Finite Element Modeling of Atherosclerotic Plaque, Proceedings of IEEE Computers in Cardiology, 791–794; Lee et al. (1996), Circumferential Stress and Matrix Metalloproteinase 1 in Human Coronary Atherosclerosis: Implications for Plaque Rupture, Atherosclerosis Thrombosis Vascular Biology, 16, 1070–1073; Vonesh et al. (1997), Regional Vascular Mechanical Properties by 3-D Intravascular Ultrasound Finite-Element Analysis, American Journal of Physiology, 272, 425–437; Beattie et al. (1999), Mechanical Modeling: Assessing Atherosclerotic Plaque Behavior and Stability in Humans, International Journal of Cardiovascular Medical Science, 2(2), 69–81; and Feezor et al. (2001), Integration of Animal and Human Coronary Tissue Testing with Finite Element Techniques for Assessing Differences in Arterial Behavior, BED-Vol. 50, 2001 Bioengineering Conference, ASME 2001. Further, these studies have indicated that such high stress regions correlate with the observed prevalence of locations of cap fracture. Moreover, it has been shown that subintimal structural features such as the thickness of the fibrous cap and the extent of the lipid core, rather than stenosis severity are critical in determining the vulnerability of the plaque. The rupture of a highly stressed fibrous cap can be prevented by using novel, interventional, therapeutic techniques such as specially designed stents that redistribute and lower the stresses in the fibrous cap.

Stents are generally tubular-shaped devices which function to hold open a segment of a blood vessel, coronary artery, or other body lumen. They are also suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. One of the advantages of the metallic stents is their high radial strength once expanded and implanted in the vessel. When a metallic stent is expanded and implanted in a coronary artery, for example, the stent typically uniformly expands forming a near perfect cylindrical shape which provides a cylindrical lumen for blood flow. The amount of stress imparted to the vessel wall from the prior art metallic stents typically is uniform at all points along the vessel wall, and in particular along the fibrous cap which retains the vulnerable plaque. Since the stresses are uniform, the fibrous cap may have a tendency to rupture since it is typically quite thin and is susceptible to the expansion forces of the stent. Thus, one disadvantage of presently designed intravascular stents is the possibility of the stent, which expands uniformly, imparting expansion forces on the fibrous cap to the degree of rupturing the cap, and inadvertently releasing the lipid pool comprising vulnerable plaque.

What has been needed and heretofore unavailable is a stent that can be used to treat a vulnerable plaque by reducing the cap stresses. The present invention satisfies this need and others.

SUMMARY OF THE INVENTION

The present invention is directed to an intravascular stent assembly that can be used to treat a lesion with vulnerable plaque by reducing the cap stresses. The invention also includes methods of using the stent assembly for the treatment of the same.

The stent assembly embodying features of the invention can be readily delivered to the desired body lumen, such as a coronary artery (peripheral vessels, bile ducts, etc.), by mounting the stent assembly on an expandable member of a delivery catheter, for example a balloon, and advancing the catheter and stent assembly through the body lumen to the target site. Generally, the stent is compressed or crimped onto the balloon portion of the catheter so that the stent assembly does not move longitudinally relative to the balloon portion of the catheter during delivery through the arteries, and during expansion of the stent at the target site. The stent is relatively flexible along its longitudinal axis to facilitate delivery through tortuous body lumens yet is stiff and stable enough radially in an expanded condition to maintain the patency of a body lumen such as an artery when implanted therein.

The stent assembly embodying features of the invention also can be a self-expanding stent made from a shape-memory alloy, such as nitinol. A self-expanding stent would be delivered via a catheter, typically without a balloon, which is generally known in the art.

In one embodiment of the invention, the tubular stent has a first section extending from one end of the stent to the other in which the undulations, bar arms and links have relatively wide cross-sections which have a greater resistance to radial expansion than narrower cross-section struts. A second section, extending from one end of the stent to the other, has undulations, bar arms and links that have cross-sections that are progressively thinner than the undulations, bar arms and links in the first section. Similarly, a third section has undulations, bar arms and links whose cross-sections are thinner than those in the first and second sections. Thus, moving from the first section to the second section and from the second section to the third section, the width of the undulations, bar arms and links progressively becomes narrower. As the stent is expanded from a crimped diameter on an expandable member or balloon of a catheter, to an implanted diameter in an artery, the third section component parts will expand more easily than those in the first section or the second section. Likewise, the component parts in the second section will expand more easily than those in the first section, but will require greater force to expand than the component parts of the third section. The expansion forces developed by the stent relative to the artery will be greatest in the third section, to a lesser degree in the second section, and will be the least in the first section. Accordingly, the first section undulations, bar arms and links are aligned with a fibrous cap so that the lesser expansion forces coincide with the fibrous cap area which will reduce the likelihood of cap rupture. In this embodiment, the radial thickness of the undulations, bar arms and links is substantially constant. Alternatively, the widths of the links can be constant in all three sections.

In another embodiment, the radial thickness of the variable components is varied in order to create asymmetrical circumferential deployment. In this embodiment, which is similar to the embodiment in which the width of the various components was varied, the radial thickness is varied, which causes portions of the stent to expand at different rates, and thus at different force concentrations. A first section has undulations, bar arms and links that have one radial thickness, and a second section has similar component parts having a radial thickness that is less than those in the first section. Likewise, a third section has undulations, bar arms and links with the smallest radial thickness. The third section, having the smallest radial thickness component parts, will expand more easily than either the first or second sections, and open the greatest amount and will impart the greatest amount of expansion force against the vessel wall. The first section undulations, bar arms and links have the greatest radial thickness and require the highest expansion forces. The third section opens the least and imparts the lowest force against the vessel, therefore it is aligned with the fibrous cap to reduce the likelihood of cap rupture.

In another embodiment of the invention, a stent is provided having cylindrical rings connected by links. At least a portion of several cylindrical rings have shortened bar arms and links relative to the length of the bar arms and links of the remaining cylindrical rings and links of the stent. Upon expansion, the shortened bar arms will require a greater force of expansion relative to the longer bar arms and links. Thus, the shorter bar arms and links are aligned with the fibrous cap since they open or expand the least and they exert a lesser amount of expansion force on the cap, thereby reducing the likelihood of cap rupture.

In one embodiment of the invention, the stent assembly includes a series of cylindrical rings formed with undulations that will straighten somewhat as the stent is expanded. The rings are axially aligned and are connected together by links to form the stent assembly. A portion of the stent will have a cover attached to the outer surface and which may extend over several of the cylindrical rings and cover a portion of an arc segment. The cover is attached to a portion of the stent either by an adhesive or by laser bonding, or some other equivalent method. As the stent expands from its delivery diameter to an implanted diameter, the cover differentially restricts the stent expansion thereby creating asymmetrical circumferential deployment. The result is that as the stent expands, the expansion forces in the area of the stent cover relative to the vessel wall are less than the expansion forces of the uncovered portion of the stent relative to the vessel wall. When the stent cover portion is aligned with the fibrous cap covering the vulnerable plaque, lower stent expansion forces are imparted to the fibrous cap, thereby reducing the likelihood of cap rupture and the lipid pool embolizing.

The presently preferred structures for the expandable cylindrical rings which form the stents of the present invention generally have a plurality of circumferential undulations containing a plurality of alternating peaks and valleys. The peaks and valleys are formed in generally U-, Y- and W-shaped patterns and aligned along the longitudinal axis. The U-shaped portions have undulations or bends that are connected to bar arms in a repeating pattern.

While the cylindrical rings and links generally are not separate structures, they have been conveniently referred to as rings and links for ease of identification. Further, the cylindrical rings can be thought of as having a series of U-, Y- and W-shaped structures in a repeating pattern. While the cylindrical rings are not divided up or segmented into U's, Y's and W's, the pattern of cylindrical rings resemble such configuration. The U's, Y's and W's promote flexibility in the stent primarily by flexing and may tip radially outwardly as the stent is delivered through a tortuous vessel. Other shapes for the undulations are equivalent and can include V shapes, keyhole shapes, zig-zags, and sinusoidal shapes.

The undulations of the cylindrical rings can have different degrees of curvature and angles of adjacent peaks and valleys to compensate for the expansive properties of the peaks and valleys. The cylindrical rings of the stents are plastically deformed when expanded (except with NiTi alloys) so that the stents will remain in the expanded condition and therefore they must be sufficiently rigid when expanded to prevent the collapse thereof in use.

With stents formed from super-elastic nickel-titanium (NiTi) alloys (nitinol), the expansion occurs when the stress of compression is removed. This allows the phase transformation from martensite back to austenite to occur, and as a result the stent expands.

After the stents are expanded some of the peaks and/or valleys may, but not necessarily, tip outwardly and embed in the vessel wall. Thus, after expansion, the stents may not have a smooth outer wall surface, rather they have small projections which embed in the vessel wall and aid in retaining the stents in place in the vessel.

The links which interconnect adjacent cylindrical rings can have a cross-section similar to the cross-sections of the undulating components of the expandable cylindrical rings. The links may be formed in a unitary structure with the expandable cylindrical rings and formed from the same intermediate product, such as a tubular element, or they may be formed independently and mechanically secured between the expandable cylindrical rings. The links may be formed substantially straight or with one or more undulations or coils. The links may also be used to support the vulnerable plaque region or to connect adjacent rings.

Preferably, the number, shape and location of the links can be varied in order to develop the desired vulnerable plaque coverage and still maintain longitudinal flexibility. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

The stent may be formed from a tube by laser cutting the pattern of cylindrical rings and links in the tube, by individually forming wire rings and laser welding them together, or by laser cutting a flat metal sheet in the pattern of the cylindrical rings and links, and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within an artery.

FIG. 2 is an elevational view, partially in section, similar to that shown in FIG. 1 wherein the stent is expanded within a diseased artery.

FIG. 3 is an elevational view, partially in section, depicting the expanded stent within the artery after withdrawal of the delivery catheter.

FIG. 9A is a plan view depicting the stent of the invention in an unexpanded configuration where the radial thickness of the struts differ around the circumference of the stent.

FIG. 9B is a cross-sectional view taken along line 9B—9B of one cylindrical ring of the stent shown in FIG. 9A showing the radial thickness of the stent struts in one cylindrical ring.

FIG. 10 is a plan view depicting a stent of the invention where at least a portion of several cylindrical rings are shorter than the other cylindrical rings of the stent.

DETAILED DESCRIPTION OF THE PREFERRED EMBODIMENTS

Figure 4:
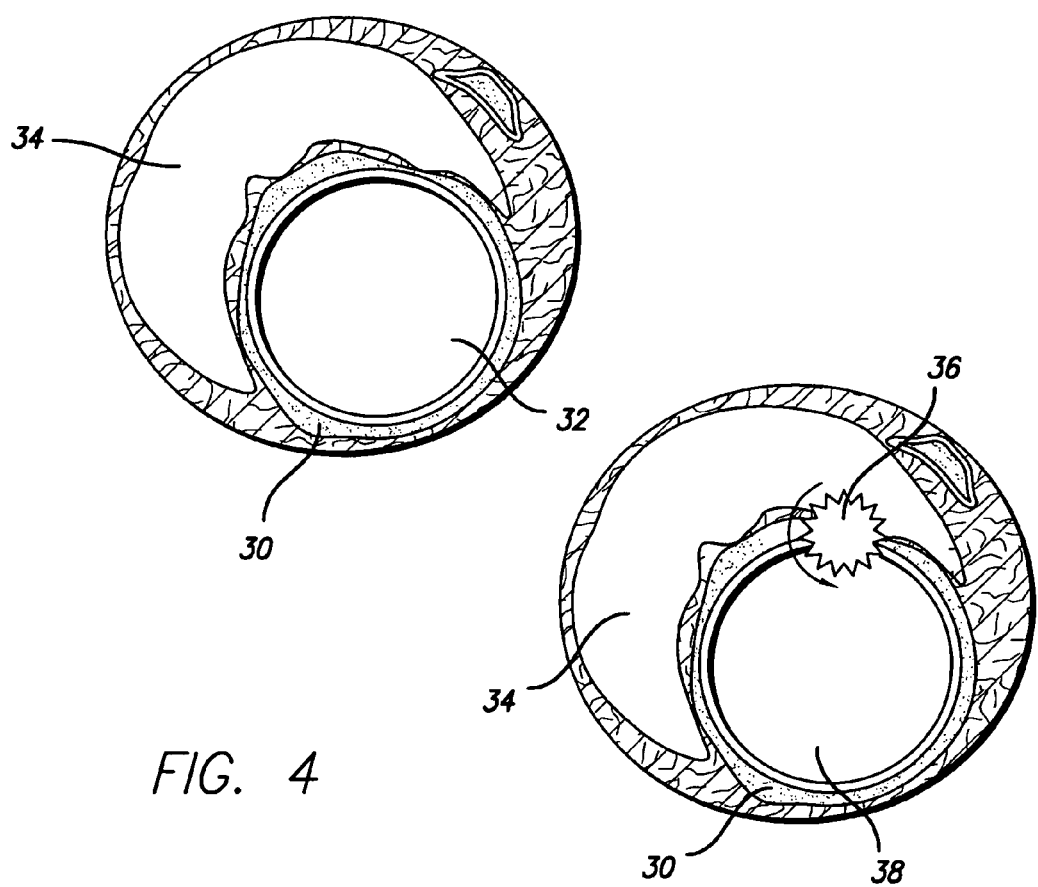
FIG. 4 is a schematic of a process of fibrous cap rupture in a fibroatheroma form of vulnerable plaque leading to a thrombotic occlusion of an artery.
Figure 5:
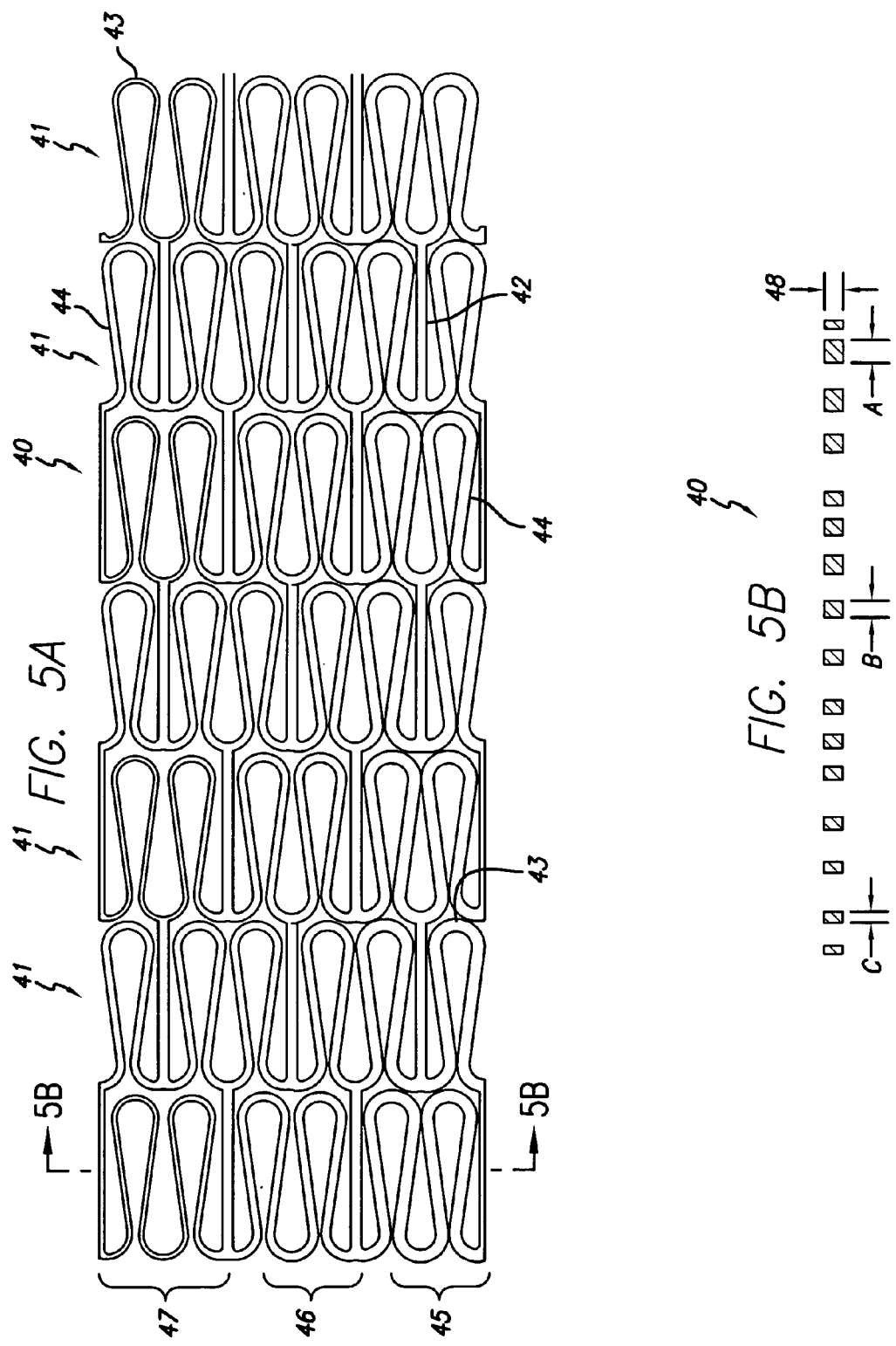
FIG. 5A is a plan view depicting the stent of the invention in an unexpanded configuration.
FIG. 5B is a cross-sectional view taken along line 5B—5B depicting the strut widths of one ring of the stent shown in FIG. 5A.

Before describing in detail an exemplary embodiment of a stent for the treatment of a vulnerable plaque in accordance with the present invention, it is instructive to briefly describe a typical stent implantation procedure and the vascular conditions which are typically treated with stents.

Turning to the drawings, FIG. 1 depicts a metallic stent 10 incorporating features of the invention mounted on a catheter assembly 12 which is used to deliver the stent and implant it in a body lumen, such as a coronary artery, peripheral artery, or other vessel or lumen within the body. The stent generally includes a plurality of radially expandable cylindrical rings 14 disposed generally coaxially and interconnected by links 16 disposed between adjacent cylindrical rings. The catheter assembly shown in FIG. 1 includes a catheter shaft 13 which has a proximal end 15 and a distal end 17. The catheter assembly is configured to advance through the patient's vascular system by advancing over a guide wire by any of the well known methods of an over the wire (OTW) system (not shown) or a well known rapid exchange (RX) catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire exits the catheter distal end 19 so that the catheter advances along the guide wire on a section of the catheter between the RX port and the catheter distal end. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the coronary arteries.

Turning to FIG. 1, a partial cross-section of an artery 24 is shown with a small amount of vulnerable plaque 25. Stent assembly 10 of the present invention is used to repair a diseased or damaged arterial wall which may include the vulnerable plaque as shown in FIG. 1. The vulnerable plaque is covered by a thin fibrous cap 30 which protects against rupture. If the fibrous cap ruptures, the vulnerable plaque comprising a lipid pool will embolize, which could prove harmful to the patient.

In a typical procedure to implant stent 10, the guide wire 18 is advanced through the patient's vascular system by well known methods so that the distal end of the guide wire is advanced past the vulnerable plaque 25 or diseased area 26. Prior to implanting the stent assembly, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent assembly is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The rings 14 and links 16 of the stent will eventually become endothelialized. It is this endothelialization and subsequent neointimal growth that will integrate the device into the fibrous cap portion of the vulnerable plaque along with the remainder of the stented portion of the artery. This integration will yield lower fibrous cap stresses overall. The undulating portion of the stent provides good tacking characteristics to prevent stent movement within the artery. Furthermore, the closely spaced cylindrical rings at regular intervals provide uniform support for the wall of the artery.

The stent patterns shown in FIGS. 1–3 are for illustration purposes only and can vary in size and shape to accommodate different vessels or body lumens. Further, the stent 10 is of a type that can be used in accordance with the present invention. Other stent configurations also are suitable for use with the present invention. For example, any tubular member having a distal and proximal end and an inner and outer wall surface extending therebetween, can be used with the present invention to create the desired asymmetrical differential deployment or focal deployment.

FIG. 4 illustrates a schematic of a process of fibrous cap rupture in a fibroatheroma form of vulnerable plaque leading to a thrombotic occlusion of an artery 24 (FIG. 1). A patent lumen 32 at the lesion site is separated from a lipid core 34 of the lesion by the fibrous cap 30. As discussed earlier, when the fibrous cap is ruptured 36, the luminal blood becomes exposed to tissue factor, a highly thrombogenic core material, which can result in total thrombotic occlusion 38 of the artery. The intravascular stent assembly of the present invention is a novel, interventional, therapeutic technique that redistributes and lowers the stresses imparted on the fibrous cap by the stent, thereby reducing the likelihood of cap rupture when the stent is implanted.

In keeping with the invention, and referring to FIGS. 5–11, the present invention stent is designed to provide a gentle deployment which will not rupture the fibrous cap with current balloon expandable stenting techniques. One way to minimize the possibility of rupturing the fibrous cap is to use an asymmetric circumferential and/or longitudinal deployment. Such a deployment requires that the stent open more on one portion of the circumference of the stent than on another portion. The portion of the stent which opens more is aligned away from the fibrous cap and the portion which minimally opens is placed directly over the cap. The minimally opening portion of the stent creates less expansion force on the fibrous cap, thereby reducing the likelihood that the forces developed during stent expansion will rupture the fibrous cap. The disclosed embodiments of the stent of the present invention will achieve asymmetric circumferential deployment, thereby reducing the stent expansion forces in the area of the fibrous cap.

Figure 8:
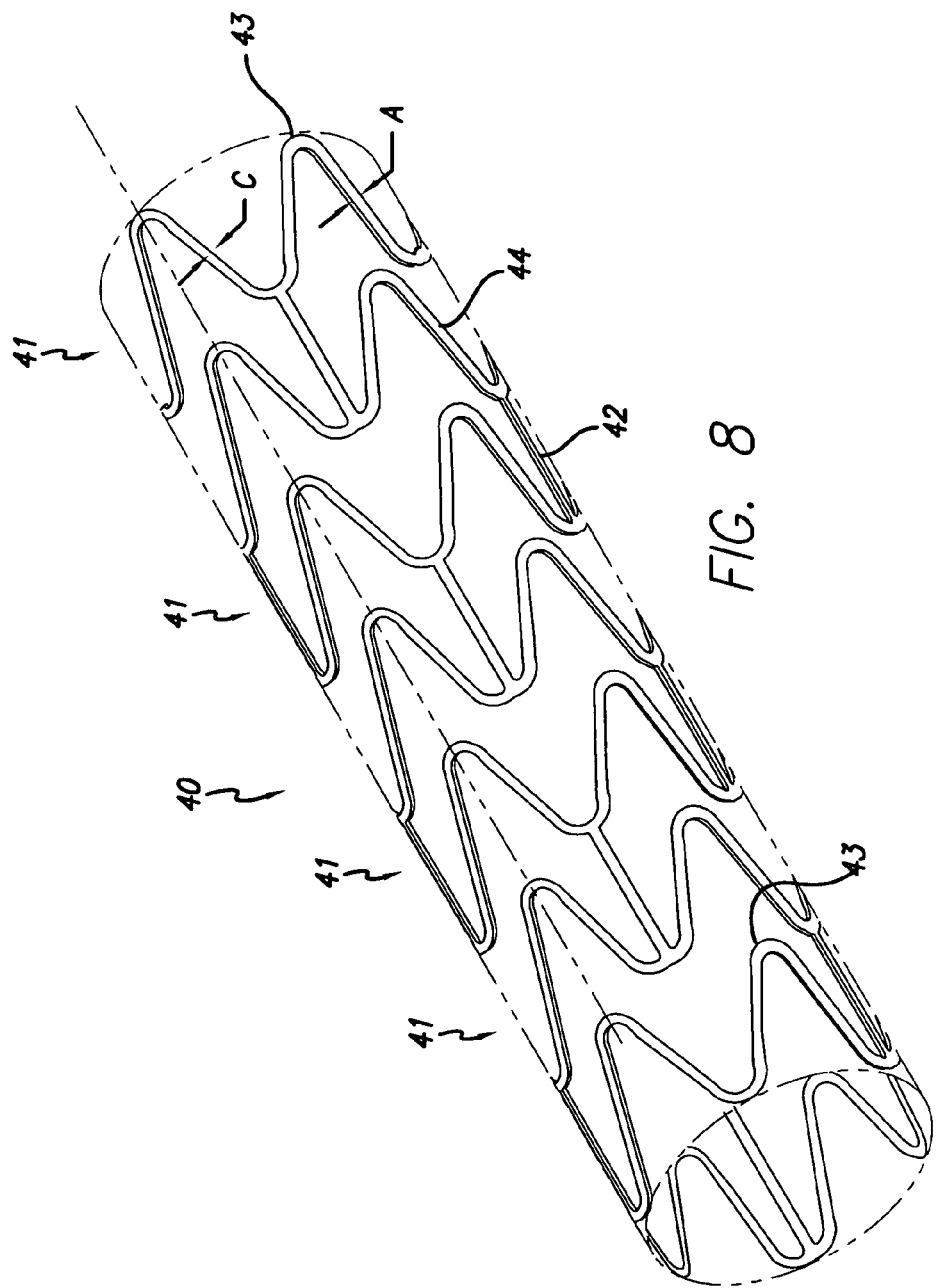
FIG. 8 is a perspective view of the stent of FIG. 7A in an expanded configuration.

In one embodiment, as shown in FIGS. 5A and 5B, a stent 40 is made from a series of cylindrical rings 41 that are connected by links 42. The cylindrical rings are made up of undulations 43 connected by bar arms 44. The stent pattern shown in FIG. 5A depicts the stent in a flattened condition so that the stent pattern can be more easily viewed. When the stent is formed in its cylindrical configuration, the undulations can be expanded significantly as shown in FIG. 8 in order to expand the stent into contact with an artery. While a particular stent pattern is shown in FIG. 5A, virtually any stent pattern can be used with the present invention to achieve the asymmetric circumferential deployment. In this embodiment, a first section 45 includes bar arms, undulations and links that have a relatively wide strut cross-section, as shown for example in FIG. 5B. A second section 46 includes bar arms, undulations and links that have cross-sections that are progressively thinner than the undulations, bar arms and links in the first section. Similarly, a third section 47 has a width of the undulations, bar arms and links that are less than those found in the first and second sections. Thus, moving from the first section to the second section, and from the second section to the third section, the width of the struts of the undulations, bar arms and links progressively becomes narrower so that the undulations, bar arms and links in the third section have the smallest width relative to the undulations, bar arms and links of the other sections. As the stent is expanded from a crimped diameter on the expandable member or balloon of the catheter to an implanted diameter in an artery, the third section component parts will expand more easily than those in the first section or second section due to their lower mass. Likewise, the component parts in the second section will expand more easily than those in the first section, but will require a greater force to expand than the component parts of the third section. Finally, the component parts of the first section, due to their greater width and mass, will require a greater expansion force than the component parts than either the second or third sections in order to expand the undulations. Similarly, as the stent expands, the expansion forces developed by the stent relative to the artery will be greatest in the first section, to a lesser degree in the second section, and will be the least in the third section. The third section undulations, bar arms and links are aligned with the fibrous cap so that the lesser expansion forces coincide with the fibrous cap area which will reduce the likelihood of rupture.

As shown in FIG. 5B, the radial thickness 48 of the undulations, bar arms and links is substantially constant, while the width A is relatively wider than width B, and width B is progressively wider than width C, which corresponds to the width described with respect to the first section 45, the second section 46 and the third section 47.

Figure 6:
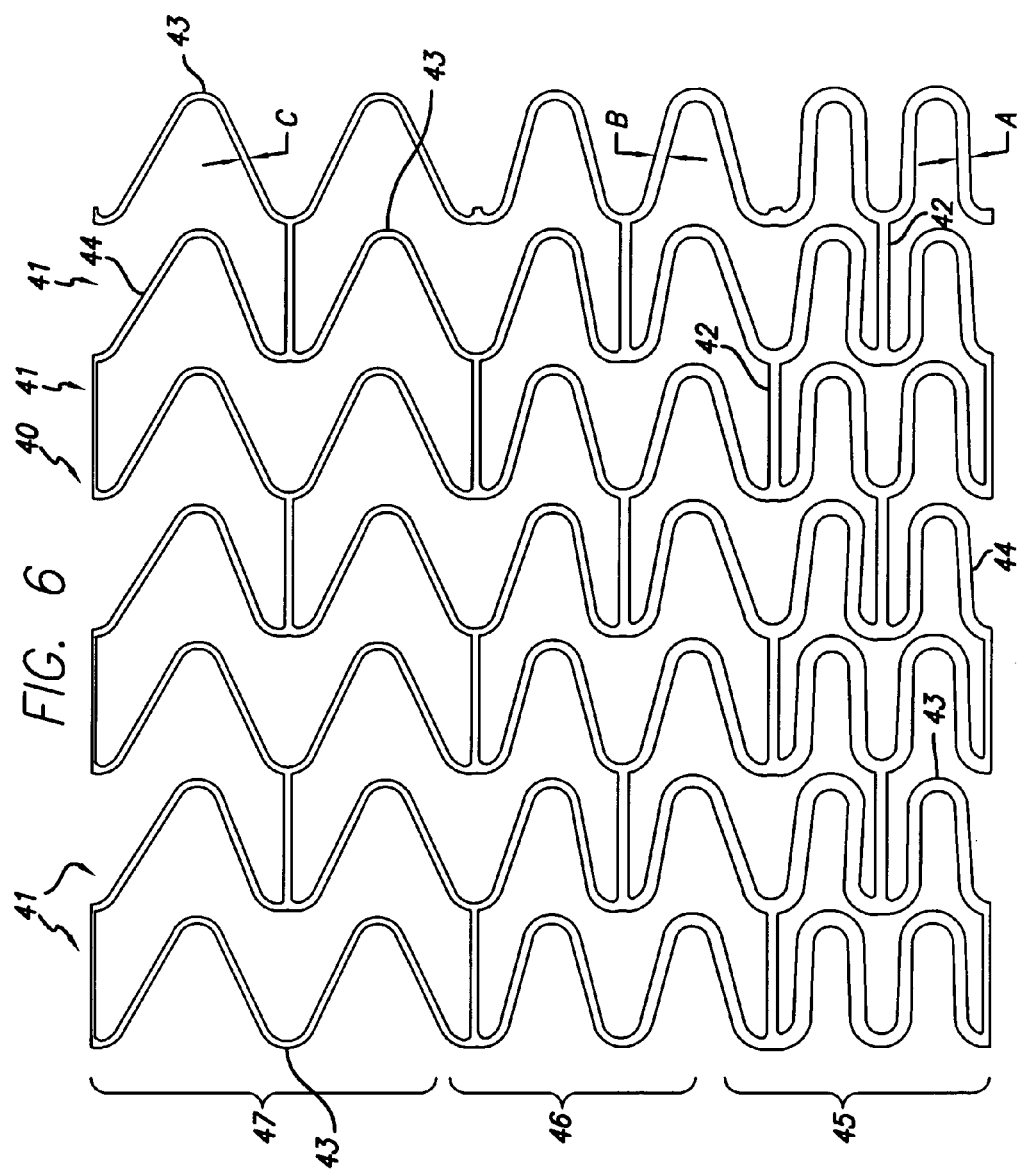
FIG. 6 is a plan view of the stent of FIG. 5 depicting an expanded stent.
Figure 7:
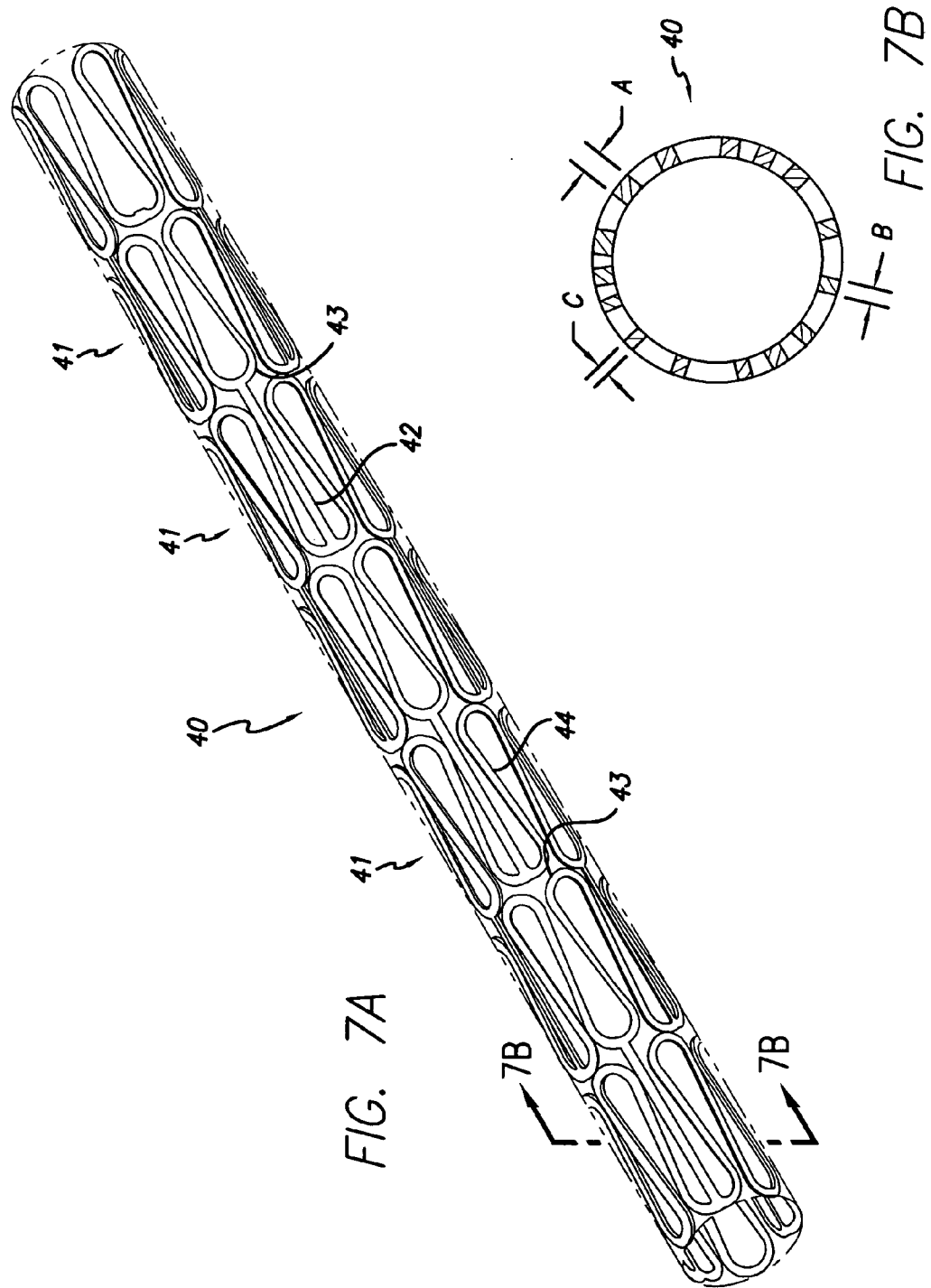
FIG. 7A is a perspective view of the stent of FIG. 5 in a cylindrical form and unexpanded.
FIG. 7B is a cross-sectional view taken along line 7B—7B depicting the strut widths of one cylindrical ring of the stent shown in FIG. 7A.

The stent shown in FIGS. 5A, 5B and 6, is shown in FIG. 7A in an unexpanded state, and in FIG. 8 in an expanded state. As would be expected, the balloon upon which the stent is mounted will expand the stent in a cylindrical fashion as shown in FIG. 8. The expanded stent will have a cylindrical configuration, but the struts and links will have an asymmetrical deployment, such as that shown in FIG. 13, i.e., focal deployment. Asymmetric circumferential deployment refers to the expansion forces developed by the stent with respect to the force imparted to the artery upon expansion and the resultant focal deployment of the struts and links. The asymmetry in the expansion forces imparted to the artery is a direct result of the stent pattern having certain stent struts that are wider than other stent struts. The wider struts will expand more slowly due to their greater mass, and will impart a lesser expansion force on the artery wall when fully expanded and implanted in an artery. As shown in FIG. 7B, the undulations, bar arms and links that have width A will impart smaller expansion forces than the undulations, bar arms and links that have width C, which is substantially thinner than the width A dimension.

In another embodiment, as shown in FIGS. 9A and 9B, a stent 60 includes a number of cylindrical rings 61 aligned along a common longitudinal axis (not shown) and connected by one or more links 62. Each of the rings includes undulations 43 that are connected by bar arms 64. The asymmetric circumferential deployment in this embodiment is achieved by varying the radial thickness of the component parts of the cylindrical rings and links. In this embodiment, the width of the undulations, bar arms and links are substantially constant, while the differences arise in the radial thickness of the various components. For example, a first section 65 extends the length of the stent and has undulations, bar arms and links that have a first radial thickness 68. A second section 66 has undulations, bar arms and links that have a second radial thickness 69, the first radial thickness being greater than the second radial thickness. A third section 67 has undulations, bar arms and links that have a third radial thickness 70, the third radial thickness being less than the second radial thickness. Thus, the radial thickness of the undulations, bar arms and links gets progressively less moving from the first section to the second section and to the third section. As shown in FIG. 9B, the width 71 of the undulations, bar arms and links in each of the first section, second section and third section is substantially constant. The undulations and bar arms in the first section will require a greater force to expand than those in the second and third sections since the radial thickness is greater in the first section than in the other two sections. Correspondingly, the expansion force that the expanded first section imparts to the artery is less than the expansion force developed in the third section, which has the smallest radial thickness undulations and bar arms. The first section 65 is accordingly aligned with the fibrous cap since it will impart the least amount of expansion forces on the fibrous cap, thereby reducing the likelihood of cap rupture.

In the embodiment shown in FIG. 10, the stent 80 contains cylindrical rings 81 that are connected by links 82. Each of the rings has undulations 83 or bends that are connected by bar arms 84. In order to achieve asymmetrical differential deployment, in this embodiment a first section 85 includes short bar arms 86 connected to the undulations and short links 87 to connect the rings. A second section 88 includes long bar arms 89 to connect the undulations and long links 90 which connect the cylindrical rings. Short bar arms 86 are shorter in length than long bar arms 89 and accordingly are less flexible and require a greater outward radial force to expand. Upon expansion by an expandable member or balloon, the first section bar arms and undulations will require a greater force to expand than the long bar arms and links in the second section. The first section, short bar arms will transmit less expansion force on the vessel since it takes more radial force to expand them. In contrast, the relatively longer bar arms require less force to expand so that they impart a greater force on the vessel wall. The first section, short bar arms that are connected to the undulations is aligned with the fibrous cap so that the force of expansion against the fibrous cap is less, thereby reducing the likelihood of cap rupture.

Figure 11:
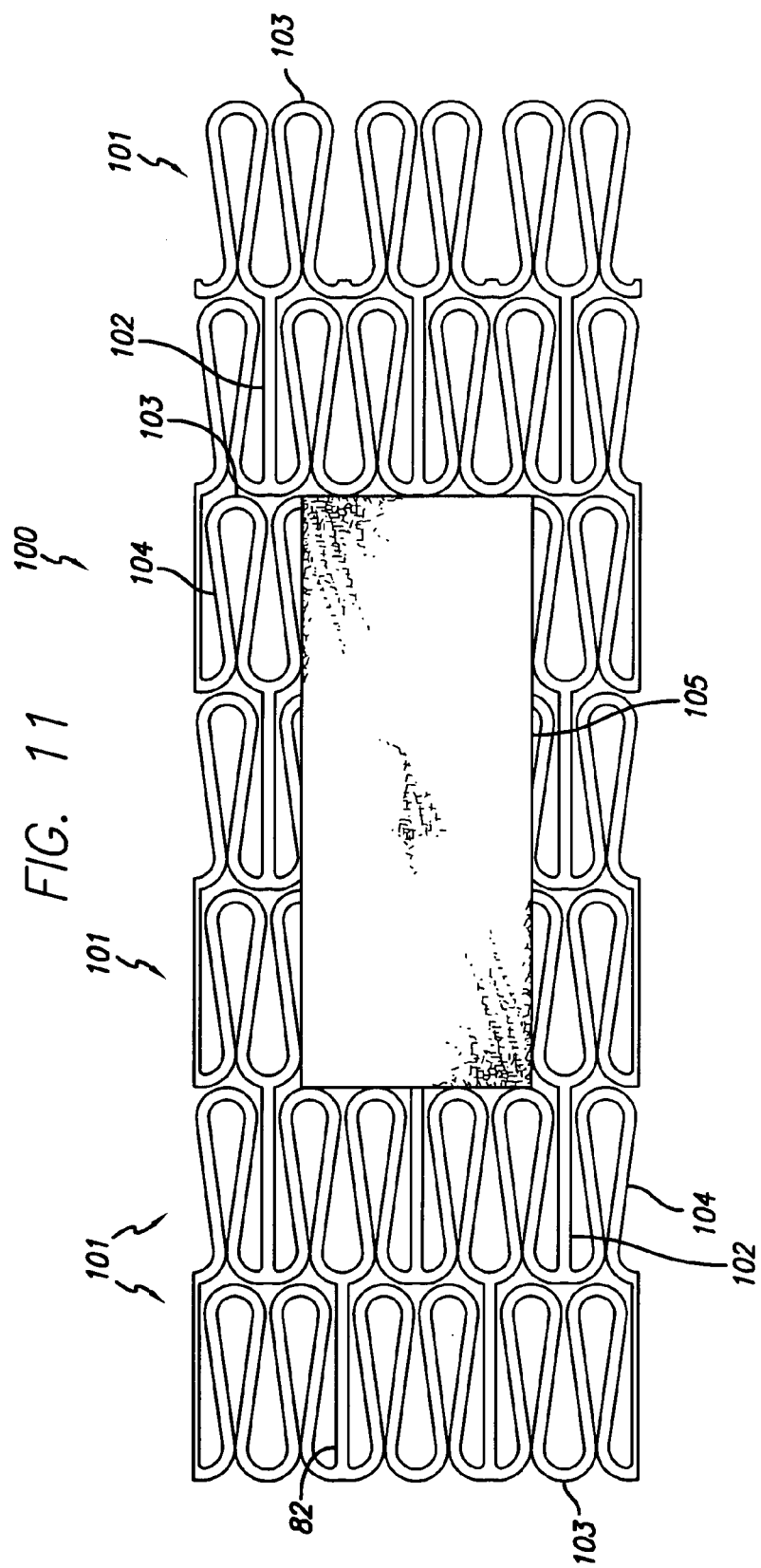
FIG. 11 is a plan view depicting the stent of the invention in an unexpanded configuration and showing a cover attached to at least a portion of the stent surface.

In another embodiment to provide for asymmetrical differential deployment, shown in FIG. 11, stent 100 includes cylindrical rings 101 aligned along a common longitudinal axis and connected by links 102. Each of the cylindrical rings includes undulations 103 or bends that are connected by bar arms 104. In keeping with the invention, a cover 105 is attached to at least a portion of the cylindrical rings and covers an arc length along the circumference of the stent. As an example, the cover extends along three cylindrical rings and extends over an arc length of less than 180°, as shown in FIG. 11. The cover can be attached to the stent outer surface by any known means such as a biocompatible adhesive, fusion bonding or an equivalent attachment means. Upon expansion of the stent from a delivery diameter to the implanted diameter, the cover 105 restricts the expansion of the undulations and bar arms that it covers so that the force required for expansion in the area of the cover is greater than the force required for expansion of the remainder of the stent. The cover restricts the expansion of the undulations in the area of the cover thereby imparting a lower expansion force to the vessel wall contacted by the cover. The stent cover is aligned with the fibrous cap so that the force of expansion against the fibrous cap is reduced, thereby reducing the likelihood of cap rupture.

The stent cover 105 can be formed of a polymer material which can include polytetrafluoroethylene (PTFE), ePTFE, fluorinated ethylene-propylene resins (FEP), fluoropolymers (TEFLON), polyethylene terephthalate (PET), Hytrel polyesters, aromatic polymers, or polyetherketone (PEEK). Other materials include block copolymers, particularly polyamide/polyester block co-polymers with a tensile strength of at least 6,000 psi, and polyamide or nylon materials, such as Nylon 12, with a tensile strength of at least 15,000 psi. Other materials useful in forming the cover can include biodegradable and bioabsorbable elastomers such as hydrogels, elastin-like peptides, polyhydroxyalkanoates (PHA's), and biodegradable polymers such as poly (lactide), poly (glycolide), and their copolymers (PLGA). Another cover material is poly (glycerol-sebacate) (PGS) (developed by Yadong Wang, MIT) and commonly referred to as biorubber. Other polymer materials include acetal copolymer/homopolymer, acrylonitrile butadiene styrene (ABS), ABS and polycarbonate, polyamide, polyimide, polyacrylate, polyaryl sulfone, polycarbonate, polyetherimide, polyether sulfone, polyphenylene oxide, polyphenylene sulfide, polypropylene, polysulfone, polyurethane, polyvinyl chloride, and styrene acrylonitrile.

The stent cover 105, as shown in FIG. 11, covers a portion of the rings both axially and circumferentially. The cover can be extended in the axial direction for the entire length of the stent or for any portion shorter than the full length of the stent in order to create the desired expansion characteristics for alignment with the fibrous cap. Also, the patch can be extended circumferentially up to approximately 180°, or less, again depending upon the size of the fibrous cap and the desired amount of restrictive characteristics on expansion. The cover material has a radial thickness in the range of 0.001 inch (0.254 mm) to 0.005 inch (0.127 mm).

In another embodiment, the cover 105 can be formed by dip coating the stent into EVAL, so that a portion of the outer surface of the stent is covered by the EVAL cover. The EVAL cover restricts expansion of the undulations 103 and bar arms 104 as previously described for FIG. 11. Thus, the EVAL cover is aligned with the fibrous cap so that the reduced expansion forces are imparted to the fibrous cap, thereby reducing the likelihood of cap rupture.

The cover 105 can be fitted with sensors (not shown) to monitor temperature or blood flow, which will give an indication of the healing process of the vessel wall surrounding the vulnerable plaque. Data collected by the sensors can be accessed remotely using ultrasound or similar known techniques.

Figure 12:
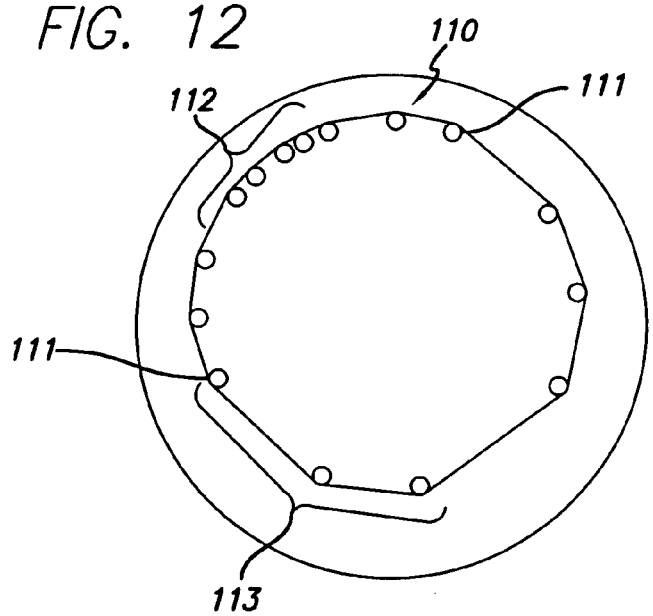
FIG. 12 is a computerized schematic of a stent with focal expansion with high strut density apposing the vulnerable plaque.

Turning to FIG. 12, a computer generated model demonstrates the focal expansion of round stent struts with high density struts apposing the fibrous cap. In the computer generated model, stent 110 is shown in cross-section where round struts 111 are concentrated in a dense pattern in first section 112 and in a less dense pattern in second section 113. The high density stent struts in the first section create a lower force of expansion and are aligned with the fibrous cap. The stent struts in the second section, upon expansion, impart a higher force of expansion and accordingly are aligned away from the fibrous cap.

Figure 13:
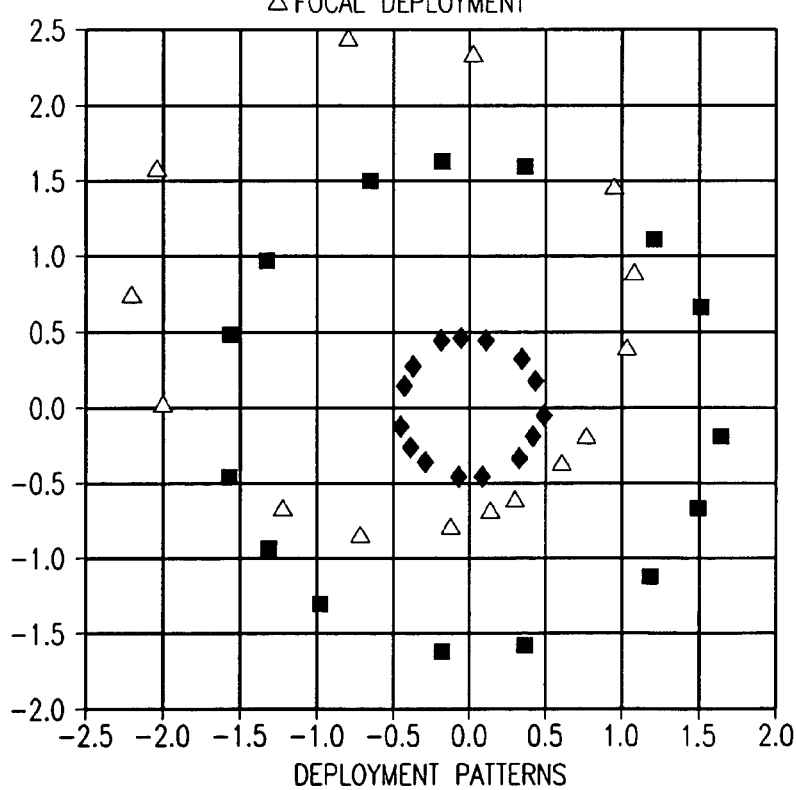
FIG. 13 is a computerized schematic showing various deployment patterns including a crimped strut distribution, a normal strut deployment, and a focal strut deployment.

Turning to FIG. 13, the computer-generated model demonstrates a normal stent deployment versus a focal or asymmetric deployment in order to protect the fibrous cap and the lipid accumulation in the area of the vulnerable plaque. As can be seen in FIG. 13, the crimped strut distribution of a stent mounted on a balloon is the same for both a normal and focal deployment stent. In other words, whether the stent is going to be deployed in a normal manner (even expansion forces against the vessel wall) or by focal deployment or asymmetrical deployment, both stents have the same crimped pattern prior to deployment. The normal deployment pattern shown in FIG. 13 shows the stent struts being uniformly distributed and approximately the same distance from the center of the crimped stent upon expansion and implanting of the stent. In contrast, a focal stent deployment, which creates a high density strut distribution over the fibrous cap (lipid pool), has a high density stent distribution in one area and a lower strut distribution in another area. In other words, the high density strut distribution over the fibrous cap significantly reduces the contact force between the stent struts and the underlying tissue within the underlying region when compared to a normal stent deployment in which there is a fairly uniform distribution of stent struts, and accordingly uniform contact force between the stent struts and the underlying tissue. The higher strut density yields a lower contact force between the stent struts within that region and the underlying tissue or vessel wall because the bulk force within that region is distributed over a larger number of struts. The reduction in the contact force between the high density strut distribution and the vessel wall in the area of the fibrous cap can reduce the likelihood that a stent strut will penetrate into the lipid core by distributing a given load over a greater number of struts within the high density region.

Several methods have been developed for assisting in aligning the stent of the present invention with the fibrous cap to ensure that the fibrous cap is not ruptured. More specifically, the vulnerable plaque region can be detected by using optical coherence tomography (OCT), which uses infrared light to locate the vulnerable plaque which reflects light differently than other tissue. An OCT apparatus can be obtained from Light Lab Imaging, Boston, Mass. Another method useful in aligning the stent of the invention with the fibrous cap and the vulnerable plaque region is by using a thermography wire. A thermography wire has a curved tip with a temperature sensor at its distal end and which is used to measure the temperature around the vessel wall. The thermography wire is highly sensitive and can distinguish slight changes in temperature. The vulnerable plaque region typically is warmer than the surrounding tissue, thus indicating the location of the vulnerable plaque so that the stent of the invention can be properly aligned.

The stent of any of the embodiments disclosed herein can be formed so that the various struts of the cylindrical rings, including the undulations, bar arms and links, all can be formed so that each has a variable radial thickness along the stent length. For example, the links may be thicker at one end than at the other end of the link. Further, the undulations may have a smaller radial thickness than the bar arms associated with the undulations. By varying the radial thickness along the length of the stent, the asymmetrical circumferential deployment can be enhanced as previously described. As an example, where the radial thickness of the undulations, bar arms or links is greatest, that portion of the stent will expand less than portions of the stent having a thinner radial thickness. Thus, the thicker radial thickness of the stent is aligned with the fibrous cap because it will impart less expansion force on the cap due to the higher mass of the stent struts.

The stents of the present invention can be made in many ways. However, the preferred method of making the stent is to cut a tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser, which is well known in the art.

The stent tubing may be made of suitable biocompatible material such as stainless steel, titanium, tungsten, tantalum, vanadium, cobalt-chromium, gold, palladium, platinum, and iradium, super-elastic (nickel-titanium) NiTi alloys and even high strength thermoplastic polymers. The stent diameters are very small, so the tubing from which it is made must necessarily also have a small diameter. For PCTA applications, typically the stent has an outer diameter on the order of about 1.65 mm (0.065 inches) in the unexpanded condition, the same outer diameter of the hypotubing from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

In the instance when the stents are made from plastic, the implanted stent may have to be heated within the arterial site where the stents are expanded to facilitate the expansion of the stent. Once expanded, it would then be cooled to retain its expanded state. The stent may be conveniently heated by heating the fluid within the balloon or the balloon itself directly by a known method.

The stents may also be made of materials such as super-elastic (sometimes called pseudo-elastic) nickel-titanium (NiTi) alloys. In this case, the stent would be formed full size but deformed (e.g. compressed) to a smaller diameter onto the balloon of the delivery catheter to facilitate intraluminal delivery to a desired intraluminal site. The stress induced by the deformation transforms the stent from an austenite phase to a martensite phase, and upon release of the force when the stent reaches the desired intraluminal location, allows the stent to expand due to the transformation back to the more stable austenite phase. Further details of how NiTi super-elastic alloys operate can be found in U.S. Pat. Nos. 4,665,906 (Jervis) and 5,067,957 (Jervis), incorporated herein by reference in their entirety.

The stent of the invention also can be coated with a drug or therapeutic agent. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, anti-platelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. An example of an immunosuppiant is tracrolimus. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. Furthermore, the calculation of dosages, dosage rates and appropriate duration of treatment are previously known in the art.

While the invention has been illustrated and described herein in terms of its use as intravascular stents, it will be apparent to those skilled in the art that the stents can be used in other instances in all vessels in the body. Since the stents of the present invention have the novel feature of enhanced longitudinal flexibility, they are particularly well suited for implantation in almost any vessel where such devices are used. This feature, coupled with limited longitudinal contraction of the stent when radially expanded, provides a highly desirable support member for all vessels in the body. Other modifications and improvements may be made without departing from the scope of the invention.

What is claimed:

1. A stent for reinforcing a fibrous cap in a body lumen, comprising:

a tubular member having a distal end, a proximal end, and an outer surface and an inner surface extending therebetween to form the stent;

a cover having a length, an arc segment, and a radial thickness;

the cover being attached to a portion of the outer surface so that as the stent expands from a first delivery diameter to a second implanted diameter the cover differentially restricts stent expansion creating asymmetrical circumferential deployment; and wherein the length of the cover is equal to the length of the stent.

2. A stent for reinforcing a fibrous cap in a body lumen, comprising:

a tubular member having a distal end, a proximal end, and an outer surface and an inner surface extending therebetween to form the stent;

a cover having a length, an arc segment, and a radial thickness;

the cover being attached to a portion of the outer surface so that as the stent expands from a first delivery diameter to a second implanted diameter the cover differentially restricts stent expansion creating asymmetrical circumferential deployment; and the stent includes a plurality of rings connected together by links and the stent rings and links have a variable radial thickness; and wherein the cover has a variable thickness that mirrors the variable thickness of the stent rings and links providing a smooth outer surface along an outer surface of the stent cover.

3. A stent for reinforcing a fibrous cap in a body lumen, comprising:
a tubular member having a distal end, a proximal end, and an outer surface and an inner surface extending therebetween to form the stent;
a cover having a length, an arc segment, and a radial thickness;
the cover being attached to a portion of the outer surface so that as the stent expands from a first delivery diameter to a second implanted diameter the cover differentially restricts stent expansion creating asymmetrical circumferential deployment; and
wherein the cover contains a sensor to measure any of temperature, blood flow, and blood pressure.

4. A stent for reinforcing a fibrous cap in a body lumen, comprising:
a tubular member having a distal end, a proximal end, and an outer surface and an inner surface extending therebetween to form the stent;
a cover having a length, an arc segment, and a radial thickness;
the cover being attached to a portion of the outer surface so that as the stent expands from a first delivery diameter to a second implanted diameter the cover differentially restricts stent expansion creating asymmetrical circumferential deployment; and
wherein the cover is formed from a metallic material taken from the group of materials consisting of stainless steel, tantalum, nickel-titanium, cobalt-chromium, titanium, platinum, and gold.

5. A stent for reinforcing a fibrous cap in a body lumen, comprising:
a plurality of cylindrical rings aligned along a common longitudinal axis, each cylindrical ring having curves and bar-arms that form undulations;
a plurality of links for connecting adjacent cylindrical rings; and
a first section and a second section;
the rings and links in the first section having a higher material density relative to the rings and links in the second section so that as the stent is expanded from a first delivery diameter to a second implanted diameter, the higher density first section differentially restricts stent expansion creating asymmetrical circumferential deployment.

6. The stent of claim 5, wherein the links and the curves and the bar-arms of the rings in the first section have a width that is greater than the width of the links, the curves and the bar-arms of the rings of the second section.

7. The stent of claim 6, wherein the width of the links and the curves and the bar-arms of the rings of the first section are progressively wider moving from a first edge of the first section to a second edge of the first section.

8. The stent of claim 5, wherein the width of the links and the curves and the bar-arms of the rings of the first section are progressively shorter moving from a first edge of the first section to a second edge of the first section.

9. The stent of claim 5, wherein the radial thickness of the links and the curves and the bar-arms of the rings of the first section are progressively thicker moving from a first edge of the first section to a second edge of the first section.

10. The stent of claim 5, wherein the number of undulations per ring in the first section is greater than the number of undulations per ring in the second section.

11. The stent of claim 5, wherein the number of links per ring in the first section is greater than the number of links per ring in the second section.

12. The stent of claim 5, wherein a cover is attached to at least a portion of the rings of the first section.

13. The stent of claim 5, wherein the first section extends circumferentially along an arc segment of less than 180°.

14. The stent of claim 5, wherein the first section extends for a length equal to the length of the stent.

15. The stent of claim 5, wherein the first segment extends for a length less then the length of the stent.

16. The stent of claim 5, wherein the curves are circumferentially spaced at uneven distances from one another.

17. The stent of claim 5, wherein at least one of the curves and bar arms has a different width than other curves and bar arms of the same ring.

18. The stent of claim 5, wherein at least one of the curves and bar arms has a different radial thickness than other curves and bar arms of the same ring.

19. The stent of claim 5, wherein each ring of the plurality of cylindrical rings has a pattern formed by the undulations, and each ring has the same pattern formed by the undulations.

20. The stent of claim 5, wherein each ring of the plurality of cylindrical rings has a pattern formed by the undulations, and at least two rings have the same pattern formed by the undulations.

21. The stent of claim 5, wherein each ring of the plurality of cylindrical rings has a pattern formed by the undulations, and at least two rings have the same pattern formed by the undulations, wherein the curves are circumferentially spaced at uneven distances from one another.

22. A method of expanding a stent to create asymmetrical circumferential deployment in a body lumen having a fibrous cap, comprising:
providing a stent having a plurality of cylindrical rings aligned along a common longitudinal axis, each ring having curves and bar-arms that form undulations, a plurality of links for connecting adjacent rings, and a first section and a second section;
the first section having a first radial force component and the second section having a second radial force component;
aligning the first section of the stent with the fibrous cap;
expanding the stent into contact with the body lumen so that the first section substantially apposes the fibrous cap and the second section apposes that portion of the body lumen away from the fibrous cap.

23. The method of claim 22, wherein the first radial force component is less than the second radial force component so that the radial force applied to the fibrous cap is less than the radial force applied to the body lumen away from the fibrous cap.

24. A stent for reinforcing a fibrous cap in a body lumen, comprising:
a tubular member having means for expanding from a first delivery diameter to a second implanted diameter;
means associated with the tubular member for creating asymmetrical circumferential deployment; and
wherein the means for creating asymmetrical differential deployment includes rings having short bar arms and rings having long bar arms, the short bar arms creating less expansion forces than the long bar arms when the stent is expanded.

* * * * *